(12) United States Patent
Jassell et al.

(10) Patent No.: US 8,726,901 B2
(45) Date of Patent: May 20, 2014

(54) VENTILATION TUBES

(75) Inventors: Surinderjit Kumar Jassell, Windsor Berkshire (GB); Kumaraguru Muthuswamy, Basingstoke Hampshire (GB)

(73) Assignee: Intersurgical AG, Vaduz (LI)

( * ) Notice: Subject to any disclaimer, the term of this patent is extended or adjusted under 35 U.S.C. 154(b) by 1356 days.

(21) Appl. No.: 12/090,572

(22) PCT Filed: Oct. 20, 2006

(86) PCT No.: PCT/GB2006/050340
§ 371 (c)(1),
(2), (4) Date: Apr. 17, 2008

(87) PCT Pub. No.: WO2007/045928
PCT Pub. Date: Apr. 26, 2007

(65) Prior Publication Data
US 2008/0251073 A1    Oct. 16, 2008

(30) Foreign Application Priority Data
Oct. 20, 2005  (GB) .................................. 0521349.1

(51) Int. Cl.
*A61M 16/08*    (2006.01)
*A61M 16/00*    (2006.01)

(52) U.S. Cl.
CPC ........... *A61M 16/0875* (2013.01); *A61M 16/08* (2013.01)
USPC ............ 128/204.17; 128/203.26; 128/203.12; 128/202.27; 128/201.13; 128/200.24

(58) Field of Classification Search
CPC . A61M 16/00; A61M 16/08; A61M 16/0816; A61M 16/0875; A61M 16/10; A61M 16/14; A61M 16/16; A61M 16/105; A61M 16/1075; A61M 2016/00; A61M 2016/08; A61M 2016/0816; A61M 2016/0883; A61M 2016/10; A61M 2016/1075; A61M 2016/108; A61M 2016/1085; A61M 2016/109; A61M 2016/1095
USPC ............. 128/200.24, 203.12, 203.16, 203.17, 128/203.26, 203.27, 204.17, 204.18, 128/204.21, 911; 156/143, 187, 188, 195, 156/244.15
See application file for complete search history.

(56) References Cited

U.S. PATENT DOCUMENTS

| 3,910,808 A | 10/1975 | Steward |
| 3,963,856 A | 6/1976 | Carlson et al. |

(Continued)

FOREIGN PATENT DOCUMENTS

| AU | 718139 B2 | 6/1997 |
| AU | 727989 B2 | 6/2000 |

(Continued)

OTHER PUBLICATIONS

International Search Report (Jan. 19, 2007) for PCT/GB2006/050340.

(Continued)

*Primary Examiner* — Annette Dixon
(74) *Attorney, Agent, or Firm* — LeClairRyan, a Professional Corporation

(57) ABSTRACT

A ventilation tube (20, 120, 220) is disclosed. The ventilation tube (20, 120, 220) comprises an inner wall (22, 122, 222) that defines a fluid passageway for 5 ventilation gases, an outer wall (24, 124, 224) that surrounds the inner wall (22, 122, 222) and has a greater thickness than the inner wall (22, 122, 222), a helical separator member (26, 126, 226) interposed between the inner and outer walls (22, 122, 222, 24, 124, 224) so as to define an insulation chamber between the inner and outer walls (22, 122, 222, 24, 124, 224), and a heating element (28, 128, 228) disposed within the insulation chamber.

49 Claims, 3 Drawing Sheets

(56) References Cited

U.S. PATENT DOCUMENTS

| | | | |
|---|---|---|---|
| 3,966,525 A | 6/1976 | Steward | |
| 4,007,737 A | 2/1977 | Paluch | |
| 4,038,519 A * | 7/1977 | Foucras | 392/472 |
| 4,172,474 A | 10/1979 | Stahl | |
| 4,233,097 A * | 11/1980 | Stahl | 156/143 |
| 4,337,800 A | 7/1982 | Carlson et al. | |
| 4,375,381 A | 3/1983 | Carlson et al. | |
| 4,459,168 A * | 7/1984 | Anselm | 156/143 |
| 4,531,551 A | 7/1985 | Eichelberger et al. | |
| 4,967,744 A * | 11/1990 | Chua | 128/204.18 |
| 5,357,948 A | 10/1994 | Eilentropp | |
| 5,454,061 A | 9/1995 | Carlson | |
| 5,630,806 A * | 5/1997 | Inagaki et al. | 604/524 |
| 5,637,168 A * | 6/1997 | Carlson | 156/143 |
| 5,640,951 A | 6/1997 | Huddart et al. | |
| 5,848,223 A | 12/1998 | Carlson | |
| 6,190,480 B1 | 2/2001 | Carlson | |
| 6,219,490 B1 | 4/2001 | Gibertoni et al. | |
| 6,367,510 B1 | 4/2002 | Carlson | |
| 6,769,431 B2 | 8/2004 | Smith et al. | |
| 7,291,240 B2 * | 11/2007 | Smith et al. | 156/195 |
| 2004/0079371 A1 | 4/2004 | Gray | |
| 2004/0099268 A1 | 5/2004 | Smith et al. | |

FOREIGN PATENT DOCUMENTS

| | | |
|---|---|---|
| CH | 220465 | 4/1942 |
| DE | 288061 | 10/1915 |
| DE | 3730551 | 3/1989 |
| DE | 20 2004 006 484 U1 | 10/2005 |
| EP | 0047185 A2 | 3/1982 |
| EP | 0201985 A1 | 11/1986 |
| EP | 0274065 A1 | 7/1988 |
| EP | 0332481 A1 | 9/1989 |
| EP | 0 672 430 A2 | 9/1995 |
| EP | 0 806 217 A2 | 11/1997 |
| EP | 0956068 B1 | 11/1999 |
| EP | 1 075 849 A2 | 2/2001 |
| EP | 1153627 A2 | 11/2001 |
| EP | 0760925 B1 | 7/2002 |
| EP | 1396276 A2 | 3/2004 |
| EP | 1741462 B1 | 1/2007 |
| GB | 2173274 A | 10/1986 |
| JP | 59049945 A | 3/1984 |
| JP | 60083871 A | 5/1985 |
| WO | 86/03362 A1 | 5/1986 |
| WO | 96/20748 A1 | 7/1996 |
| WO | 97/18001 A1 | 5/1997 |
| WO | 03/055554 A1 | 7/2003 |

OTHER PUBLICATIONS

Written Opinion of the International Searching Authority for PCT/GB2006/050340.

Search Report (Jan. 15, 2007) for Great Britain Patent Application No. 0620820.1, which claims benefit of priority to Great Britain Patent Application No. 0521349.1.

* cited by examiner

VENTILATION TUBES

This application is a U.S. national stage entry of International Patent Application Number PCT/GB2006/050340, filed 20 Oct. 2006, which claims priority From Great Britain Patent Application No. 0521349.1, filed 20 Oct. 2005.

This invention relates to ventilation tubes, and in particular to ventilation tubes for use in respiratory circuits for ventilating patients.

FIELD OF THE INVENTION

Background of the Invention

In a healthy person the function of breathing is entirely spontaneous. The brain senses a build-up of carbon dioxide in the blood and immediately calls for more oxygen. This oxygen is taken into the body by spontaneous inspiration and carbon dioxide is removed in the passive exhalation phase of respiration.

The upper airway of a healthy person functions to filter, warm and humidify inspired air, and in turn to capture heat and moisture during expiration. It is essential that the humidity within the upper airway is maintained at a sufficiently high level to ensure efficient gas exchange, and to maintain the mucociliary transport system. The mucociliary transport system is responsible for trapping inhaled contaminants and removing them from the lung. Compromised mucociliary transport can result in reduced airway patency and lung compliance, and can increase the risk of infection.

When a patient is ventilated using a respiratory circuit, the upper airway is often bypassed using an endrotracheal tube, further reducing the ability to humidify inspired air. However, a sufficient humidity can be achieved using conventional apparatus, such as a heat-moisture exchanger (HME) or a heated water bath humidifier. In the case of a heated water bath, as humid inspiratory gas travels along the respiratory circuit, a certain amount of water vapour will cool and start to condense, forming water droplets, which will start to build up, causing so-called "rain-out". A quantity of rain-out indicates a reduction in humidity delivery to the patient and excess rain-out can cause occlusion of the ventilation tube, and potentially damage the ventilator or anaesthetic equipment.

This water may occlude the respiratory air flow or drain back into the patient's lungs thereby putting the patient at risk of drowning, and may also drain into the ventilator/anaesthetic equipment thus causing damage. If water is allowed to accumulate over a prolonged period then due to its non-compressible nature the water will effectively block the respiratory circuit.

In order to reduce the build-up of condensed water within a respiratory circuit, ventilation tubes have been developed that include means for heating the tube. Such ventilation tubes reduce cooling of the water vapour within the respiratory circuit, and hence reduce the amount of water vapour that condenses to form water droplets.

Conventionally, the means for heating the ventilation tube comprises a heating element of resistively-heated wire that is generally located either within the fluid passageway of the ventilation tube, or embedded within a support bead extending about the exterior of the ventilation tube. However, none of these prior art arrangements has been found to be entirely satisfactory.

In particular, a heating element that is located within the fluid passageway of the ventilation tube may disrupt airflow along the ventilation tube and/or become damaged during use. Embedding the heating element within a support bead of the ventilation tube addresses these disadvantages, but such ventilation tubes are relatively inefficient at heating the fluid passageway. In particular, a large proportion of the heat generated by the heating element is generally lost through the external surface of the ventilation tube. Consequently, the external surface of the ventilation tube may have a temperature that could present a hazard to patients and/or medical staff.

There has now been devised an improved ventilation tube, an improved method of manufacturing a ventilation tube, and improved apparatus for manufacturing a ventilation tube, which overcome or substantially mitigate the above-mentioned and/or other disadvantages associated with the prior art.

SUMMARY OF THE INVENTION

According to a first aspect of the invention, there is provided a ventilation tube for use in a respiratory circuit, the ventilation tube comprising an inner wall that defines a fluid passageway for ventilation gases, an outer wall that surrounds the inner wall and has a greater thickness than the inner wall, a helical separator member interposed between the inner and outer walls so as to define an insulation chamber between the inner and outer walls, and a heating element disposed within the insulation chamber.

The ventilation tube according to the invention is advantageous principally because the heating element is disposed externally of the fluid passageway so that the fluid passageway is not obstructed, and the fluid passageway and heating element are both insulated from the surroundings by the insulation chamber so as to reduce heat loss from the ventilation tube and reduce the temperature of the exterior surfaces of the ventilation tube. The outer wall having a greater thickness than the inner wall causes the heat generated by the heating element to be transferred preferentially through the inner wall into the fluid passageway of the ventilation tube, rather than through the outer wall into the surroundings. Furthermore, this feature provides structural strength for the ventilation tube, which enables the inner wall to have a reduced thickness, and hence a greater rate of heat transfer into the fluid passageway, than prior art ventilation tubes.

The heating element is preferably in contact with the inner wall, preferably along a majority of its length and most preferably along its entire length. Furthermore, the heating element preferably extends along the entire length of the ventilation tube. The heating element is preferably bonded to the inner wall of the ventilation tube, most preferably along at least a majority of its length, so as to facilitate heat transfer into the fluid passageway. However, the heating element may simply be wound about the inner wall, without any bonding between the heating element and the inner wall.

The insulation chamber preferably extends along a helical path about the inner wall and fluid passageway. The helical separator member is preferably bonded to an exterior surface of the inner wall and an interior surface of the outer wall, and preferably defines a boundary of the insulation chamber. In particular, the boundaries of the insulation chamber are preferably defined by an exterior surface of the inner wall, an interior surface of the outer wall, and facing surfaces of adjacent laps of the helical separator member. The helical separator member preferably has the form of a bead of plastics material, and is preferably formed of extruded plastics material. In presently preferred embodiments, the helical separator member is formed of the same material as the inner and outer walls, so that the helical separator member is readily bonded to the inner and outer walls during manufacture.

The heating element preferably includes an electrical conductor that has a resistance sufficient for the electrical conductor to generate and emit heat when a suitable potential difference is applied across it. The electrical conductor is preferably encapsulated within an electrically-insulating material, such as a plastics material. In presently preferred embodiments, the electrically-insulating material is the same as the material of the inner wall so that the heating element may be readily bonded to the inner wall during manufacture, as discussed in more detail below. The heating element may include more than one electrical conductor, and in this case the electrically-insulating material preferably insulates the electrical conductors from one another. Most preferably, the electrical conductor has the form of a wire.

In presently preferred embodiments, the heating element comprises two electrical conductors in the form of wires, which are arranged adjacent and parallel to each other. At one end of the heating element, the wires are preferably electrically connected to each other, and at the other end of the heating element the wires preferably each have a free end that is connectable to a suitable electrical connector. Each wire is preferably encapsulated within an electrically-insulating material, and most preferably a unitary body of electrically-insulating material encapsulates both wires. The unitary body of electrically-insulating material preferably includes a portion of reduced thickness between the two wires so that the free ends of the wires can be readily separated, and the separated free ends of the wires are preferably readily connectable to appropriate terminals of the electrical connector. In particular, the free ends of the wires are preferably readily separable so that the separated free ends of the wires are each encapsulated within electrically-insulating material, and a portion of that material may be removed so as to enable connection to the electrical connector. Being able to readily separate the free ends of the wires before connection to appropriate terminals of the electrical connector reduces the risk of a short circuit occurring during connection.

In presently preferred embodiments, the ventilation tube is provided with one or more tubular connectors. Each tubular connector is preferably formed at an end of the ventilation tube, and is adapted to connect the fluid passageway of the ventilation tube to a fluid passageway of another component of a respiratory circuit. In addition, the ventilation tube preferably includes at least one tubular connector having an electrical connector that enables the heating element to be connected to a suitable power source. For example, the electrical connector may have the form of a plug socket including termination pins.

The inner and outer walls are preferably both generally tubular in form, with an annular cross-section, and are preferably formed of plastics material. Most preferably, the inner and outer walls are each formed from an extruded tape of plastics material. In particular, an extruded tape of plastics material is preferably helically wound with each lap of the tape having a trailing edge that overlaps a leading edge of the preceding lap. The overlapping edges of the first tape are preferably heat-bonded together so as to form a lap joint. This is most preferably achieved by helically winding the first tape whilst it has a sufficiently elevated temperature for the overlapping edges of the first tape to become heat-bonded together.

According to a further aspect of the invention, there is provided a method of manufacturing a ventilation tube for use in a respiratory circuit, the method comprising the following steps:

(a) forming an inner wall that defines a fluid passageway for ventilation gases,
(b) forming a helical separator member on an exterior surface of the inner wall;
(c) locating a heating element alongside the inner wall, and
(d) forming an outer wall that surrounds and has a greater thickness than the inner wall so as to define an insulation chamber between the inner and outer walls within which is disposed the heating element, steps (b) and (c) being performed in any order or substantially simultaneously.

According to a related aspect of the invention, there is provided apparatus for the manufacture of a ventilation tube for use in a respiratory circuit, the apparatus comprising means for forming an inner wall that defines a fluid passageway for ventilation gases, means for forming a helical separator member on an exterior surface of the inner wall; means for locating a heating element alongside the inner wall, and means for forming an outer wall that surrounds and has a greater thickness than the inner wall so as to define an insulation chamber between the inner and outer walls within which is disposed the heating element.

The method and apparatus according to the invention are advantageous principally because the ventilation tube formed by the method or using the apparatus offers the advantages discussed above. In addition, however, the heating element is incorporated within the ventilation tube during formation of the fluid passageway so that no additional manufacturing steps are necessary to locate the heating element appropriately within the ventilation tube, and the method and apparatus may be less complex than methods and apparatus that involve embedding the heating element within a support bead of the ventilation tube.

The method and apparatus according to the invention are preferably adapted to form a ventilation tube as described above.

The inner wall of the ventilation tube may be formed by any suitable method. However, the inner wall is preferably formed from a first tape of plastics material, which is preferably formed by extrusion from a first extrusion unit. In particular, the first tape is preferably helically wound about an external surface of a mandrel, such that each lap of the first tape has a trailing edge that overlaps a leading edge of a preceding lap. The overlapping edges of the first tape are preferably heat-bonded together so as to form a lap joint. This is most preferably achieved by helically winding the first tape whilst it has a sufficiently elevated temperature for the overlapping edges of the first tape to become heat-bonded together. Similarly, the outer wall is preferably formed from a second tape of plastics material, which is preferably formed by extrusion from a second extrusion unit, as discussed in more detail below.

In presently preferred embodiments, the separator member is formed by extrusion of a plastics material from a third extrusion unit, and the separator member is helically wound about the inner wall before the outer wall is formed. The separator member is preferably heat-bonded to the inner wall. This is most preferably achieved by helically winding the separator member about the inner wall whilst the separator member and the inner wall have a sufficiently elevated temperature for the separator member and the inner wall to become heat-bonded together. The separator member preferably has the form of a bead of plastics material.

The heating element is preferably wound, from a spool or the like, helically about the inner wall. Most preferably, the heating element is wound about the inner wall whilst the inner wall has a sufficiently elevated temperature for the heating element to become bonded to the inner wall once the inner wall has cooled. Alternatively, however, the heating element may be wound about the inner wall once the inner wall has cooled, such that the heating element does not become bonded to the inner wall.

The heating element preferably includes one or more electrical conductors that each have a resistance sufficient for the electrical conductor to generate and emit heat when a suitable potential difference is applied across it. The electrical conductor(s) are preferably encapsulated within a suitable electrically-insulating material, such as a plastics material. Most preferably, the electrically-insulating material is formed about the electrical conductor(s) and allowed to cool before the heating element is wound about the inner wall.

In order that the heating element is disposed within the insulation chamber defined between the inner and outer walls, the heating element is preferably wound between adjacent laps of the separator member. However, the separator member and the heating element may be wound in any order, or substantially simultaneously.

As described above, the outer wall is preferably formed from a second tape of plastics material. In particular, the second tape is preferably helically wound over the separator member with a first lap of the second tape overlying adjacent laps of the separator member, and subsequent laps of the second tape having a leading edge overlying the separator member and a trailing edge overlapping a leading edge of the preceding lap of the second tape. The overlapping edges of the second tape and the separator member are preferably heat-bonded together so as to form a lap joint of the outer wall that is bonded to the separator member. This is most preferably achieved by helically winding the second tape whilst the second tape, and preferably also the separator member, have a sufficiently elevated temperature for the second tape and the separator member to become heat-bonded together.

The ventilation tube is preferably formed about a mandrel. The mandrel is preferably generally cylindrical, and is preferably rotated, in use, about a central longitudinal axis whilst the first tape, second tape, separator member, and/or heating element, are wound about the mandrel. In addition, in order to achieve the helical winding of the first tape, second tape, separator member, and/or heating element, the mandrel preferably moves relative to the extrusion unit(s) and/or heating element spool along a central longitudinal axis of the mandrel. This may be achieved by either moving the mandrel, or alternatively moving the extrusion unit(s) and/or the heating element spool in unison.

The ventilation tube is preferably formed with at least one tubular connector that is adapted to connect the fluid passageway of the ventilation tube to a fluid passageway of another component of a respiratory circuit. The inner and outer walls, the separator member, and the heating element, are preferably therefore cut to an appropriate length, and a tubular connector is connected to one, or each, end of the inner and outer walls. The tubular connector may be injection moulded directly onto the outer wall, once the outer wall has cooled, in a process commonly referred to as "overmoulding". Alternatively, however, the connector may be fixed to the ventilation tube using a suitable adhesive.

The ends of the heating element may then be prepared for connection to a suitable power source. The heating element preferably comprises two electrical conductors in the form of wires, which are arranged adjacent and parallel to each other. Most preferably, the two wires of the heating element are connected together at one end of the ventilation tube, and connected to a suitable electrical connector at the other end of the ventilation tube.

Each wire is preferably encapsulated within an electrically-insulating material, and most preferably a unitary body of electrically-insulating material encapsulates both wires. The unitary body of electrically-insulating material preferably includes a portion of reduced thickness between the two wires so that the free ends of the wires can be readily separated, and the separated free ends of the wires are preferably readily connectable to appropriate terminals of the electrical connector. In particular, the free ends of the wires are preferably separated so that the separated free ends of the wires each remain encapsulated within electrically-insulating material, and a portion of that material is removed so as to enable connection to the electrical connector. Being able to readily separate the free ends of the wires before connection to appropriate terminals of the electrical connector reduces the risk of a short circuit occurring during connection. The electrical connector preferably includes termination pins to which the wires are connected, and the electrical connector preferably forms part of the tubular connector. The electrical connector may have any suitable form, such as a plug socket.

BRIEF DESCRIPTION OF THE DRAWINGS

Preferred embodiments of the invention will now be described in greater detail, by way of illustration only, with reference to the accompanying drawings, in which.

DETAILED DESCRIPTION OF THE INVENTION

Figure 1:
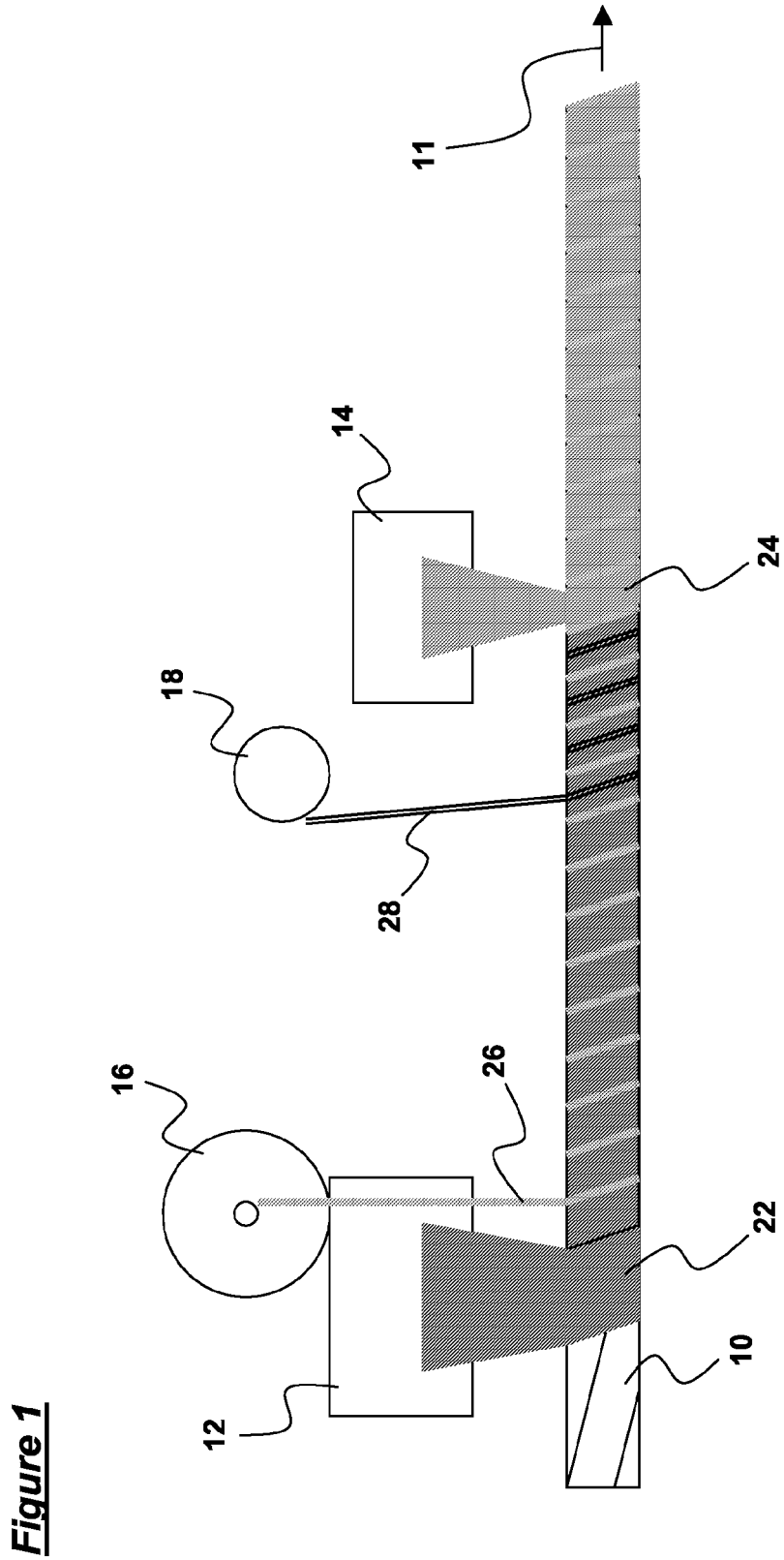
FIG. 1 is a schematic diagram showing apparatus according to the invention, and illustrating a method according to the invention.

The apparatus according to the invention shown in FIG. 1 comprises a mandrel 10, a first extrusion unit 12 for forming a first tape of plastics material, a second extrusion unit 14 for forming a second tape of plastics material, with a thickness that is greater than that of the first tape, a third extrusion unit 16 for forming a separator member having the form of a bead of plastics material 26, and a spool 18 from which a heating element 28 is unwound. The first tape, second tape, and bead 26 are each formed of plastics material having a sufficiently elevated temperature for the plastics material to be extrudable and for various components to become heat-bonded, as described in more detail below. One suitable plastics material for the first and second tapes, and the bead 26, is polyvinylchloride.

The mandrel 10 is a cylindrical rod that is rotatable about a central longitudinal axis, and is also adapted for linear movement along that axis, as shown by reference numeral 11. The first extrusion unit 12 is arranged relative to the mandrel 10 so that the first tape of plastics material exits the unit 12, in use, along a direction that is substantially perpendicular to the mandrel 10.

The first tape of plastics material is laid on the mandrel 10 as the mandrel 10 is rotated and advanced along its central longitudinal axis, so that the tape becomes helically wound about the mandrel 10 with a trailing edge of each lap of the tape overlapping a leading edge of the preceding lap. This arrangement is achieved by controlling the relative speeds at which the first tape exits the first extrusion unit 12, and at which the mandrel 10 is linearly advanced. During this step, the overlapping edges of the first tape are at a sufficiently elevated temperature to become heat-bonded together, so as to form a helical lap joint. In this way, a cylindrical inner wall 22 of plastics material is formed about the mandrel 10.

The third extrusion unit 16 is arranged so that the bead of plastics material 26 exits the unit 16, in use, along a direction that is substantially perpendicular to the mandrel 10, and the bead 26 is laid on the exterior surface of the inner wall 22 of plastics material. In particular, the bead 26 is laid on the exterior surface of the inner wall 22 as the inner wall 22 is carried by the rotating and advancing mandrel 10, so that the bead 26 becomes helically wound about the inner wall 22, and extends along the helical lap joint formed by the overlapping edges of the first tape of the inner wall 22. During this step, the bead 26 and the exterior surface of the inner wall 22 are both at a sufficiently elevated temperature to become heat-bonded together.

The spool 18 is arranged so that the heating element 28 is laid on the exterior surface of the inner wall 22 as the inner wall 22 is carried by the rotating and advancing mandrel 10, so that the heating element 28 becomes helically wound about the inner wall 22, and extends along a central axis of the first tape of plastics material, approximately equidistant from, and parallel to, adjacent laps of the bead 26. During this step, the exterior surface of the inner wall 22 is at a sufficiently elevated temperature for the heating element 28 to become heat-bonded to it.

The heating element 28 comprises a pair of electrically-conductive wires that have a resistance sufficient for the wires to generate and emit heat by application of a suitable potential difference across the wires. The pair of wires extend along the length of the heating element 28, and are arranged adjacent and parallel to one another. The wires are encapsulated within a unitary body of a relatively soft insulation material, such as a plastics material, and hence are insulated. The insulation material also insulates the wires from one another along the length of the heating element 28. Furthermore, the unitary body of insulation material includes a portion of reduced thickness between the two wires so that the free ends of the wires can be readily separated. In particular, the insulation material has a cross-section with a generally figure-of-eight configuration.

The insulation material is formed about the wires and allowed to cool before the heating element 28 is wound about the inner wall 22. However, since the exterior surface of the inner wall 22 is at a sufficiently elevated temperature, as discussed above, the heating element 28 becomes heat-bonded to the inner wall 22 during this step. Furthermore, the insulation material is the same material as that of the first tape of plastics material, in order to further facilitate the formation of a heat-bond between the heating element 28 and the inner wall 22.

The second tape of plastics material from the second extrusion unit 14 is then laid helically over the bead 26. In particular, the second tape of plastics material is laid on the bead 26 as the inner wall 22, bead 26 and heating element 28 are carried by the rotating and advancing mandrel 10, so that the second tape becomes helically wound over the bead 26 with a first lap of the second tape overlying adjacent laps of the bead 26, and subsequent laps of the second tape having a leading edge overlying the bead 26 and a trailing edge overlapping a leading edge of the preceding lap. During this step, the bead 26 and the overlapping edges of the second tape are all at a sufficiently elevated temperature to become heat-bonded together, so as to form a helical lap joint that is bonded to the bead 26. In this way, a generally cylindrical outer wall 24 is formed. The second tape is of greater thickness than the first tape and so the outer wall 24 has a greater thickness than that of the inner wall 22.

The arrangement is such that the inner wall 22, outer wall 24, and bead 26, together define an air-filled insulation chamber 23.

Once the mandrel 10 carries a desired length of ventilation tube, the first and second tapes, the bead 26 and the heating element 28 are cut. The ventilation tube is then cooled using conventional means. On cooling, the overlapping edges of each of the first and second tapes become securely bonded to each other so as to form generally cylindrical inner and outer walls 22,24. In addition, the bead 26 and heating element 28 become securely bonded to the exterior surface of the inner wall 22, and the outer wall 24 becomes securely bonded to the bead 26. Once the ventilation tube has cooled sufficiently, it is removed from the mandrel 10 and subjected to whatever further manufacturing steps, eg trimming, fitting of end connectors etc, are necessary for its intended application.

A first embodiment of a ventilation tube according to the invention, manufactured using the method discussed above, is shown in FIGS. 2 and 3, and is generally designated 20. For clarity, only a short length of ventilation tube 20 is shown. In practice, ventilation tubes according to the invention will have a length that will generally be considerably greater than that shown in FIGS. 2 and 3.

The ventilation tube 20 comprises a generally cylindrical inner wall 22, a generally cylindrical outer wall 24, with a thickness that is greater than that of the inner wall 22, a helical bead 26 that separates the inner and outer walls 22,24, and a heating element 28 bonded to the outer surface of the inner wall 22.

An insulation chamber 23 is defined between the inner and outer walls 22,24 and the bead 26. The insulation chamber 23 extends helically about the fluid passageway defined by the inner wall 22, along the entire length of the ventilation tube 20. Since the heating element 28 is in contact with the inner wall 22 along its entire length, the heating element 28 will transfer the majority of the heat generated to the inner wall 22, which is more heat-conductive than the air within the insulation chamber 23. The heated inner wall 22 will in turn transfer its heat to the ventilation gases and water vapour flowing through the fluid passageway of the ventilation tube 20. Furthermore, the insulation chamber 23 will reduce the amount of heat that is transferred to the outer wall 24 of the ventilation tube 20, and hence will reduce the amount of heat that is lost to the surroundings and would otherwise create a hazard for patients and medical staff. This decreased loss of heat due to the insulating chamber results in lower "rain-out" within the fluid passageway of the ventilation tube 20, resulting in increased humidity delivery to the patient.

Figure 4:
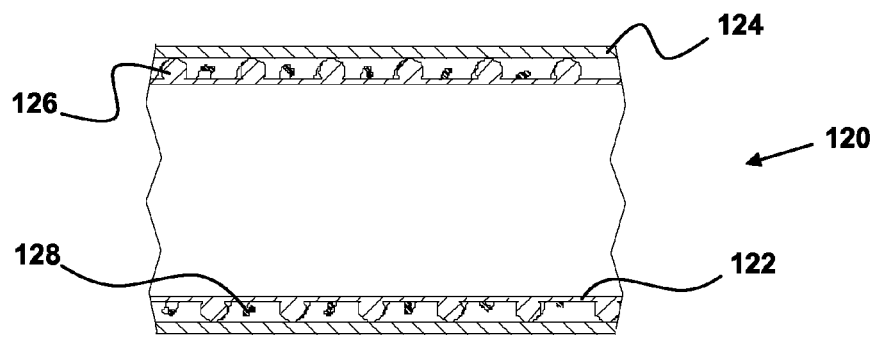
FIG. 4 is a cross-sectional view of a short length of a second embodiment of a ventilation tube according to the invention.

A second embodiment of a ventilation tube according to the invention is shown in FIG. 4, and is generally designated 120. Again, for clarity, only a short length of ventilation tube 120 is shown. In practice, ventilation tubes according to the invention will have a length that will generally be considerably greater than that shown in FIG. 4.

This ventilation tube 120 is identical to the ventilation tube 20 of the first embodiment save for the heating element 128 of the second embodiment being only loosely wound about the inner wall 122, rather than being bonded thereto. The method of manufacturing this ventilation tube 120 differs from the method discussed above in that a generally conventional ventilation tube is firstly formed, which comprises the inner wall 122 and bead 126 of the ventilation tube 120 only. The inner wall 122 and bead 126 of the ventilation tube 120 are allowed to cool before the heating element 128 is helically wound about the inner wall 122, and then the outer wall 124 is formed.

As for the first embodiment, the insulation material is formed about the wires of the heating element 128 and allowed to cool before the heating element 128 is wound about the inner wall 122. Hence, since the exterior surface of the inner wall 22 has also been allowed to cool, as discussed above, the heating element 28 does not become heat-bonded to the inner wall 22.

As discussed above in relation to the method and apparatus according to the invention, the heating elements 28,128 of the first and second embodiments each comprise a pair of electrically-conductive wires that have a resistance sufficient for the wires to be heated by application of a potential difference across the wires. At one end of the ventilation tube 20,120 the ends of the wires are generally connected together, and at the other end of the ventilation tube 20,120 the ends of the wires are generally adapted for connection to a power source in a manner that is suitable for its particular application. In particular, the free ends of the wires are readily separable so that the separated free ends of the wires each remain encapsulated within insulation material, and a portion of that material may be removed so as to enable connection to an electrical connector or power source. Being able to readily separate the free ends of the wires before connection to appropriate terminals of an electrical connector or power source reduces the risk of a short circuit occurring during connection.

Figure 2:
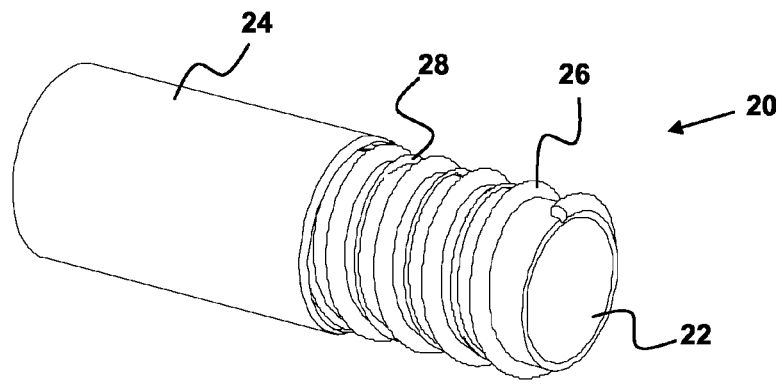
FIG. 2 is a perspective view, partially cut-away, of a short length of a first embodiment of a ventilation tube according to the invention.
Figure 3:
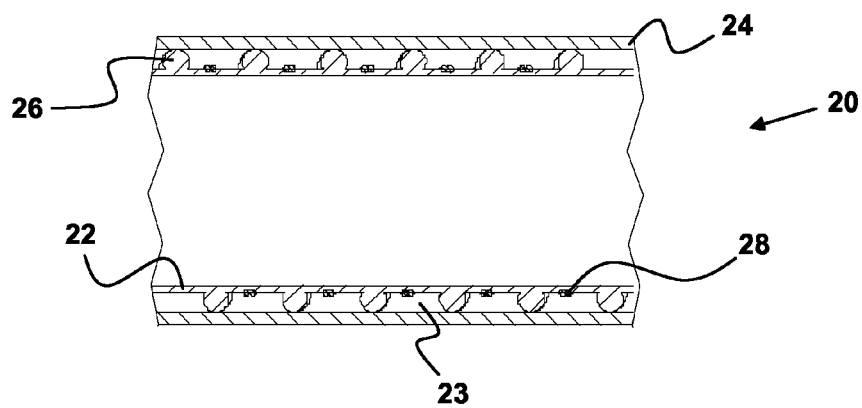
FIG. 3 is a cross-sectional view of the ventilation tube of FIG. 2.
Figure 5:
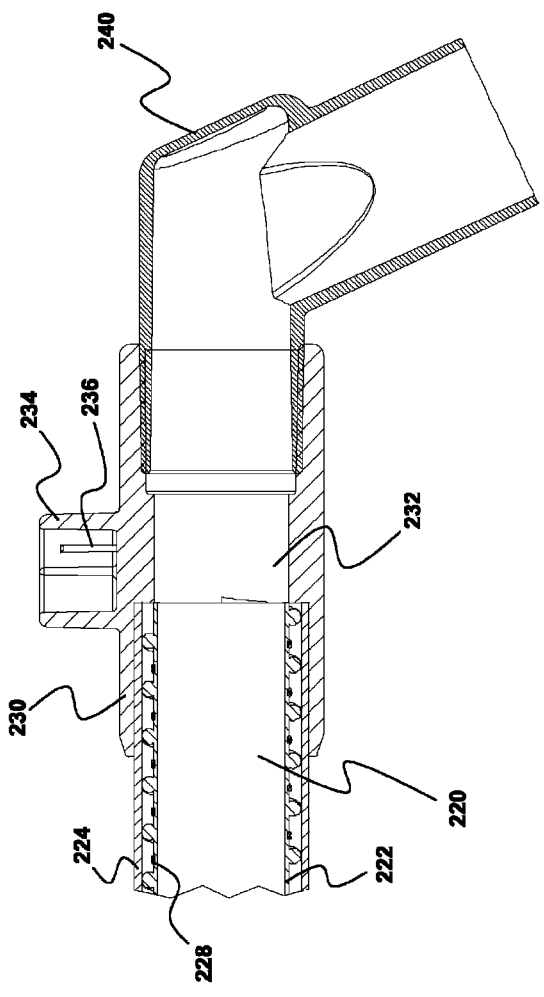
FIG. 5 is a cross-sectional view of one end of a ventilation tube of the type shown in FIGS. 2 and 3, to which is fitted a tubular connector.

FIG. 5 shows, in cross-section, one end of a completed ventilation tube 220 of the type shown in FIGS. 2 and 3, and to which is fitted a tubular connector 230 that enables connection of the fluid passageway of the ventilation tube 220 to another component of a respiratory circuit, and also connection of the heating element 228 to a suitable power source.

The tubular connector 230 has an internal bore 232 that defines a fluid passageway through the tubular connector 230, and a conventional cloverleaf electrical plug socket 234. The internal bore 232 includes an annular recess at one end, in which the inner and outer walls 222,224 are received so that the inner wall 222 is substantially aligned with the interior surface of the remainder of the internal bore 232. The other end of the internal bore 232 has a gradually increasing diameter towards its entrance, so that a female connecting portion is formed. In FIG. 5, the female connecting portion is shown engaged with a male connecting portion of an angled elbow connector 240.

The tubular connector 230 is injection moulded in a plastics material directly on to the external surface of the outer wall 224, in a process commonly referred to as "overmoulding", such that the outer wall 224 becomes bonded to the interior surface of the annular recess of the tubular connector 230.

Before injection moulding of the tubular connector 230 at which the heating element 228 will be connected to a power source, the free ends of the wires of the heating element 228 are separated so that the separated free ends of the wires each remain encapsulated within insulation material, and a portion of each of those free ends is stripped of insulation material. Once the tubular connector has been injection moulded, the socket 234 is completed by joining the stripped portions of the wires of the heating element 228 to a pair of termination pins 236, which are then arranged appropriately within the socket 236. The joining of the termination pins 236 and the stripped portions of the wires of the heating element 228 is preferably achieved by a crimp and contact arrangement, but may also be achieved by soldering.

The invention claimed is:

1. A ventilation tube for use in a respiratory circuit, the ventilation tube comprising an inner wall that defines a fluid passageway for ventilation gases, an outer wall that surrounds the inner wall and has a greater thickness than the inner wall, a helical separator member interposed between the inner and outer walls so as to define an insulation chamber between the inner and outer walls, and a heating element disposed within the insulation chamber, wherein the fluid passageway and heating element are both insulated from the surroundings by the insulation chamber.

2. A ventilation tube as claimed in claim 1, wherein the heating element is in contact with the inner wall.

3. A ventilation tube as claimed in claim 2, wherein the heating element is in contact with the inner wall along a majority of its length.

4. A ventilation tube as claimed in claim 3, wherein the heating element is in contact with the inner wall along its entire length.

5. A ventilation tube as claimed in claim 1, wherein the heating element is bonded to the inner wall of the ventilation tube.

6. A ventilation tube as claimed in claim 5, wherein the heating element is bonded to the inner wall of the ventilation tube along at least a majority of its length.

7. A ventilation tube as claimed in claim 1, wherein the heating element is wound about the inner wall, without any bonding between the heating element and the inner wall.

8. A ventilation tube as claimed in claim 1, wherein the helical separator member is bonded to an exterior surface of the inner wall and an interior surface of the outer wall.

9. A ventilation tube as claimed in claim 8, wherein the helical separator member has the form of a bead of plastics material.

10. A ventilation tube as claimed in claim 1, wherein the helical separator member is formed of the same material as the inner and outer walls.

11. A ventilation tube as claimed in claim 1, wherein the heating element includes an electrical conductor that has a resistance sufficient for the electrical conductor to generate and emit heat when a suitable potential difference is applied across it.

12. A ventilation tube as claimed in claim 11, wherein the electrical conductor is encapsulated within an electrically-insulating material.

13. A ventilation tube as claimed in claim 12, wherein the electrically-insulating material is the same as the material of the inner wall.

14. A ventilation tube as claimed in claim 11, wherein the electrical conductor has the form of a wire.

15. A ventilation tube as claimed in claim 14, wherein the heating element comprises two electrical conductors in the form of wires, which are arranged adjacent and parallel to each other.

16. A ventilation tube as claimed in claim 15, wherein the wires are electrically connected to each other at one end of the heating element, and the wires each have a free end that is connectable to a suitable electrical connector at the other end of the heating element.

17. A ventilation tube as claimed in claim 16, wherein each wire is encapsulated within an electrically-insulating material.

18. A ventilation tube as claimed in claim 17, wherein a unitary body of electrically-insulating material encapsulates both wires.

19. A ventilation tube as claimed in claim 18, wherein the unitary body of electrically-insulating material includes a portion of reduced thickness between the two wires so that the free ends of the wires can be readily separated.

20. A ventilation tube as claimed in claim 1, wherein the ventilation tube is provided with one or more tubular connectors.

21. A ventilation tube as claimed in claim 20, wherein the ventilation tube includes at least one tubular connector having an electrical connector that enables the heating element to be connected to a suitable power source.

22. A ventilation tube as claimed in claim 1, wherein the inner and outer walls are both generally tubular in form, with an annular cross-section.

23. A ventilation tube as claimed in claim 1, wherein the boundaries of the insulation chamber are defined by an exterior surface of the inner wall, an interior surface of the outer wall and facing surfaces of adjacent laps of the helical separator member.

24. A method of manufacturing a ventilation tube for use in a respiratory circuit, the method comprising the following steps:
   (a) forming an inner wall that defines a fluid passageway for ventilation gases;
   (b) forming a helical separator member on an exterior surface of the inner wall;
   (c) locating a heating element alongside the inner wall; and
   (d) forming an outer wall that surrounds and has a greater thickness than the inner wall so as to define an insulation chamber between the inner and outer walls within which is disposed the heating element;
   steps (b) and (c) being performed in any order or substantially simultaneously, wherein the fluid passageway and heating element are both insulated from the surroundings by the insulation chamber.

25. A method as claimed in claim 24, wherein the method is adapted to form a ventilation tube as defined in claim 1.

26. A method as claimed in claim 24, wherein the inner wall is formed from a first tape of plastics material that is helically wound about an external surface of a mandrel, such that each lap of the first tape has a trailing edge that overlaps a leading edge of a preceding lap.

27. A method as claimed in claim 26, wherein the overlapping edges of the first tape are heat-bonded together so as to form a lap joint by helically winding the first tape whilst it has a sufficiently elevated temperature for the overlapping edges of the first tape to become heat-bonded together.

28. A method as claimed in claim 26, wherein the outer wall is formed from a second tape of plastics material that is helically wound over the helical separator member with a first lap of the second tape overlying adjacent laps of the helical separator member, and subsequent laps of the second tape having a leading edge overlying the helical separator member and a trailing edge overlapping a leading edge of the preceding lap of the second tape.

29. A method as claimed in claim 28, wherein the overlapping edges of the second tape and the helical separator member are heat-bonded together, by helically winding the second tape whilst the second tape and the helical separator member have a sufficiently elevated temperature for the second tape and the helical separator member to become heat-bonded together, so as to form a lap joint of the outer wall that is bonded to the helical separator member.

30. A method as claimed in claim 24, wherein said forming the helical separator member comprises extruding a plastics material, and helically winding the extruded plastics material about the inner wall to form the helical separator member before the outer wall is formed.

31. A method as claimed in claim 30, wherein the helical separator member is heat-bonded to the inner wall by helically winding the extruded plastics material about the inner wall whilst the extruded plastics material and the inner wall have a sufficiently elevated temperature for the helical separator member and the inner wall to become heat-bonded together.

32. A method as claimed in claim 24, wherein the heating element is wound helically about the inner wall.

33. A method as claimed in claim 32, wherein the heating element is wound about the inner wall whilst the inner wall has a sufficiently elevated temperature for the heating element to become bonded to the inner wall once the inner wall has cooled.

34. A method as claimed in claim 32, wherein the heating element is wound between adjacent laps of the helical separator member.

35. A method as claimed in claim 24, wherein the inner and outer walls, the helical separator member, and the heating element, are cut to an appropriate length, and a tubular connector is connected to one, or each, end of the inner and outer walls.

36. A method as claimed in claim 35, wherein the tubular connector is injection moulded directly onto the outer wall, once the outer wall has cooled.

37. A method as claimed in claim 24, wherein the ends of the heating element are prepared for connection to a suitable power source.

38. A method as claimed in claim 37, wherein the heating element comprises two electrical conductors in the form of wires, which are arranged adjacent and parallel to each other, and the two wires of the heating element are connected together at one end of the ventilation tube, and connected to a suitable electrical connector at the other end of the ventilation tube.

39. A method as claimed in claim 38, wherein the electrical connector forms part of the tubular connector.

40. A method as claimed in claim 24, wherein the boundaries of the insulation chamber are defined by an exterior surface of the inner wall, an interior surface of the outer wall and facing surfaces of adjacent laps of the helical separator member.

41. Apparatus for the manufacture of a ventilation tube for use in a respiratory circuit, the apparatus comprising means for forming an inner wall that defines a fluid passageway for ventilation gases, means for forming a helical separator member on an exterior surface of the inner wall, means for locating a heating element alongside the inner wall, and means for forming an outer wall that surrounds and has a greater thickness than the inner wall so as to define an insulation chamber between the inner and outer walls within which is disposed the heating element are both insulated from the surroundings by the insulation chamber.

42. Apparatus as claimed in claim 41, wherein the apparatus is adapted to form a ventilation tube as defined in claim 1.

43. Apparatus as claimed in claim 41, wherein the apparatus has a mandrel and a first extrusion unit for extruding a first tape of plastics material, the apparatus being adapted to helically wind the first tape about an external surface of the mandrel, such that each lap of the first tape has a trailing edge that overlaps a leading edge of a preceding lap, so as to form the inner wall.

44. Apparatus as claimed in claim 43, wherein the apparatus has a second extrusion unit for extruding a second tape of plastics material, and the apparatus is adapted to helically wind the second tape over the helical separator member with a first lap of the second tape overlying adjacent laps of the helical separator member, and subsequent laps of the second tape having a leading edge overlying the helical separator member and a trailing edge overlapping a leading edge of the preceding lap of the second tape.

45. Apparatus as claimed in claim 44, wherein the apparatus has a third extrusion unit for extruding a member formed of a plastics material, the apparatus being adapted to helically wind the member about the inner wall, before the outer wall is formed, to form the helical separator member.

46. Apparatus as claimed in claim 43, wherein the apparatus has a spool or the like from which the heating element is wound helically about the inner wall.

47. Apparatus as claimed in claim 43, wherein the mandrel is generally cylindrical and is rotated about a central longitudinal axis whilst the first tape, the second tape, a member for forming the helical separator member, and/or the heating element, are wound about the mandrel.

48. Apparatus as claimed in claim 47, wherein the mandrel moves relative to the extrusion unit(s) and/or heating element spool along a central longitudinal axis of the mandrel.

49. An apparatus as claimed in claim 41, wherein the boundaries of the insulation chamber are defined by an exterior surface of the inner wall, an interior surface of the outer wall and facing surfaces of adjacent laps of the helical separator member.

* * * * *